US00PP25011P3

(12) United States Plant Patent
Brown

(10) Patent No.: US PP25,011 P3
(45) Date of Patent: Oct. 28, 2014

(54) ***CALLISTEMON VIMINALIS* PLANT NAMED 'LC01'**

(50) Latin Name: *Callistemon viminalis*
Varietal Denomination: LC01

(71) Applicant: Graham Brown, Pennant Hills (AU)

(72) Inventor: Graham Brown, Pennant Hills (AU)

( * ) Notice: Subject to any disclaimer, the term of this patent is extended or adjusted under 35 U.S.C. 154(b) by 107 days.

(21) Appl. No.: 13/694,475

(22) Filed: Dec. 5, 2012

(65) Prior Publication Data

US 2014/0157466 P1 Jun. 5, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Sam McCoy

(57) ABSTRACT

'LC01' is a distinctive variety of *Callistemon viminalis* which is characterized by the combination of a short to medium height, large leaves, deep green foliage, large inflorescence, and stability and uniformity of traits through successive cycles of asexual propagation.

3 Drawing Sheets

Latin name of the genus and species: The Latin name of the genus and species of the novel variety disclosed herein is *Callistemon viminalis*.

Variety denomination: The inventive variety of *Callistemon viminalis* disclosed herein has been given the variety denomination 'LC01'.

The present application claims priority from a provisional U.S. application No. U.S. 61/567,236 filed Dec. 6, 2011, which is herein incorporated by reference.

BACKGROUND OF THE INVENTION

The present invention relates to a new and distinct perennial variety of *Callistemon viminalis*, which has been given the variety denomination of 'LC01'. Its market class is that of an ornamental tree or shrub. 'LC01' is intended for use in landscaping as a small tree or hedge shrub.

Parentage: The *Callistemon viminalis* variety 'LC01' was the result of a controlled pollination between seed parent *Callistemon viminalis* 'x2003.1.1' (unpatented) and pollen *Callistemon viminalis* 'x2003.1.3' (unpatented) in September 2005 at a commercial plant breeding facility in Cobbitty in the state of New South Wales, Australia. These parents were, themselves, progeny of a previous cross pollination of two well known forms of *Callistemon* which are *Callistemon viminalis* 'Captain Cook' (unpatented) and *Callistemon viminalis* 'Little John' (unpatented). Both parents exhibited an intermediate size, improved vigor and improved flower habit. Resultant seed from the controlled pollination of 2005 were collected and germinated during 2006 and transplanted to the field in 10 cm pots in September of 2006. Initial selection took place in September 2009 on the criteria of more compact and bushy habit, deep green foliage and a superior flower display compared to that of the parent plants and also other seedling accessions from the same parent cross. In 2010 trials and evaluation continued including confirmation of DUS (Distinctness, Uniformity and Stability) and commercial propagation by cuttings. The cultivar was named 'LC01'.

Asexual Reproduction: 'LC01' is propagated asexually by division. The distinctive characteristics of the inventive 'LC01' variety are stable from generation to generation; clones of the variety produced by asexual reproduction maintain the distinguishing characteristics of the original plant.

SUMMARY OF THE INVENTION

'LC01' is a distinctive variety of *Callistemon viminalis* which is characterized by the combination of a short to medium height, an erect to semi erect shrub habit and a high flower density.

BOTANICAL DESCRIPTION OF THE PLANT

Figure 1:
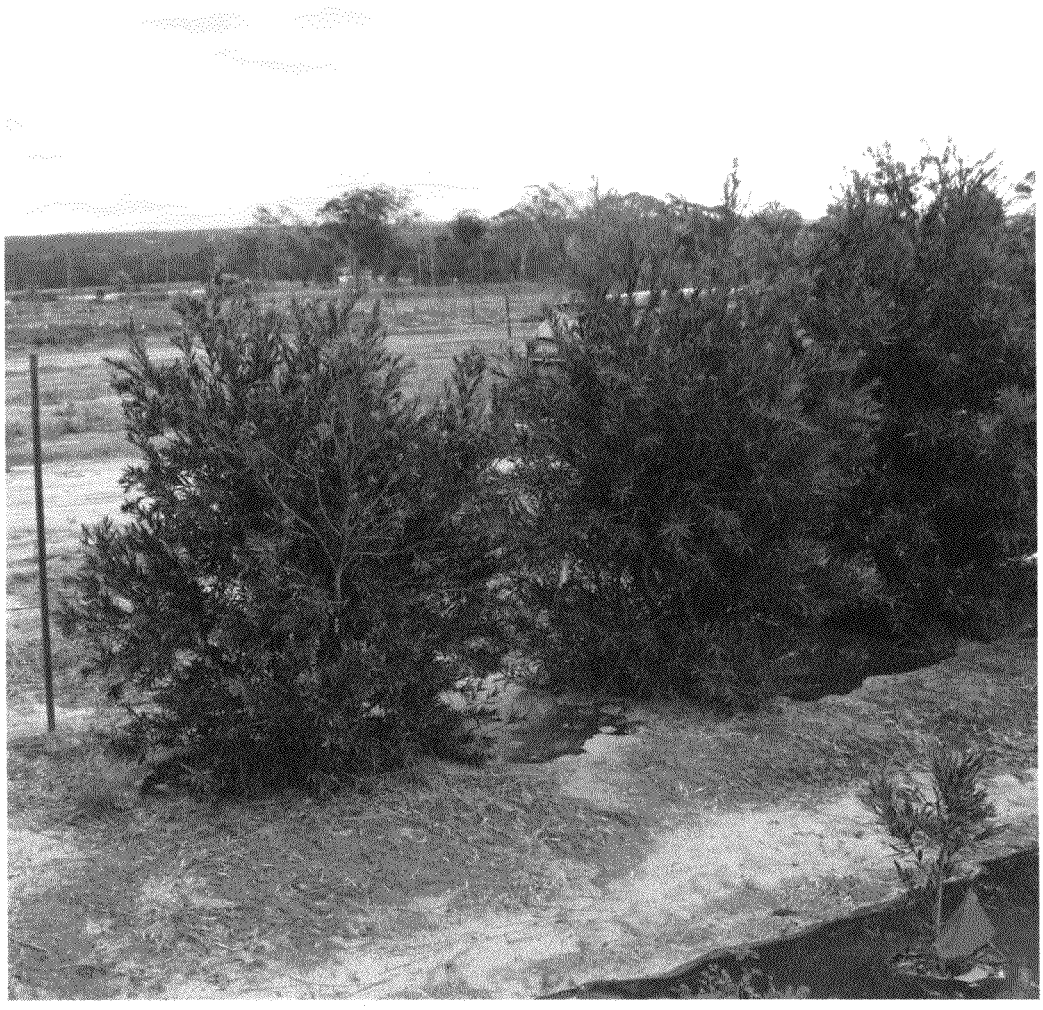
FIG. 1 shows a 'LC01' plant, at far left, in the ground and unpruned, at approximately 3 years old with other F1 seedling accessions from the same parent cross for comparison.
Figure 2:
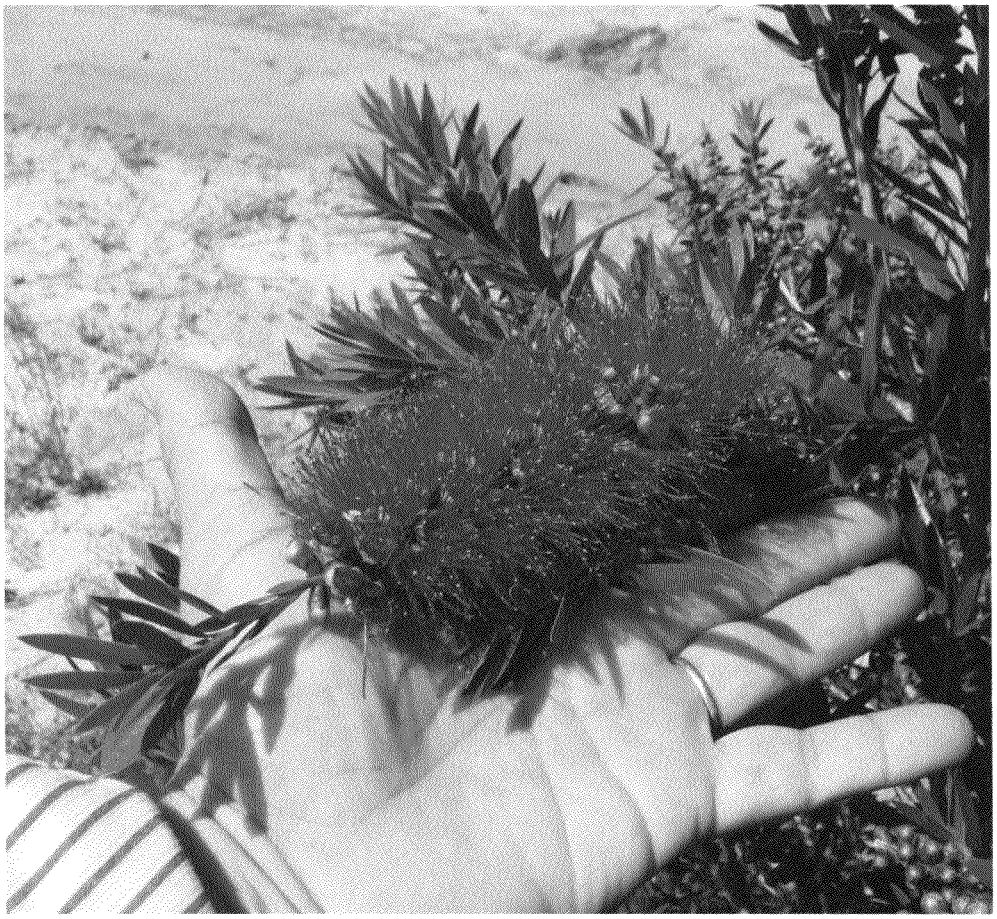
FIG. 2 shows a typical inflorescence spike
Figure 3:
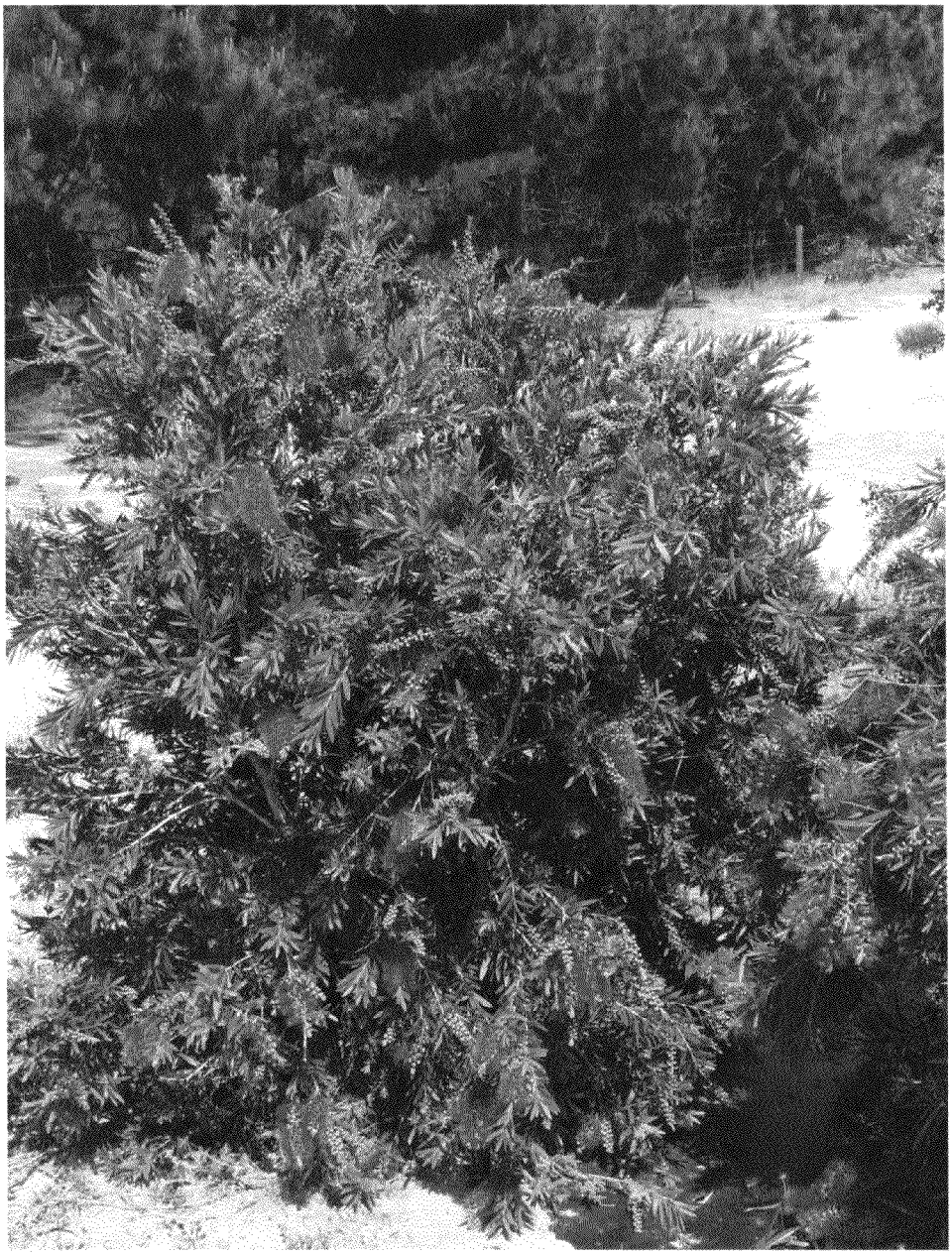
FIG. 3 shows the same 'LC01' plant illustrated in FIG. 1 at approximately 4 years old, in bloom.

The following is a detailed botanical description of a new and distinct variety of *Callistemon viminalis* known as 'LC01' based upon observations of 24-month old plants grown from rooted cuttings into 200 mm nursery pots in full sun in open beds in Clarendon, New South Wales, Australia during spring 2009 to summer 2010. Unless indicated otherwise, the descriptions disclosed herein are based upon observations made from mature 'LC01' plants grown in full sun from rooted cuttings filled with soilless potting media, maintained with granular slow release fertilizer, and regularly watered with overhead irrigation. No pest and disease measures were taken. Observation data was recorded in summer of 2010.

Those skilled in the art will appreciate that certain characteristics will vary with older or, conversely, with younger plants. 'LC01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2001 edition.

A botanical description of 'LC01' and comparisons with other varieties of *Callistemon viminalis* are provided below.

TECHNICAL DESCRIPTION OF THE VARIETY

Plant description:

*Plant habit*.—Shrub; erect to semi erect, rounded and dense:

*Height*.—180 cm at maturity.

*Width*.—150 cm at maturity.

*Bloom period*.—Spring.

*Hardiness*.—USDA Zone 8 to 11.

*Environmental tolerances*.—Similar to the parent plants; tolerates light shade, a wide range of soil conditions and drought tolerant once established.

*Pest and disease susceptibility or resistance*.—In common with the species, none of note.

*Propagation*.—Propagation is accomplished using softwood cuttings. Roots well without rooting compound or hormone.

*Time to develop roots*.—2 to 4 weeks.

*Crop time*.—Approximately 12 months are needed to produce a 14-centimeter container with plant in flower, starting from a rooted cutting.

Stem

*Branching and habit*.—Strong branching habit; branch angles acute, branch attitude is erect to semi erect.

*Stem strength*.—Woody and strong.

*Shape*.—Cylindrical.

*Stem color*.—Immature stem is closest to greyed orange RHS 164A. Mature basal stem color is closest to grey brown RHS 199D.

*Stem dimensions*.—Basal stems reach approximately 27 to 32 cm in length before branching; diameter is approximately 7 mm near the base.

*Stem surface*.—Corky, smooth. Immature stems are highly pubescent while mature stems are lightly pubescent to glabrous.

*Internode length*.—Ranges from 10 to 15 mm.

Foliage:

*Type*.—Evergreen.

*Shape*.—Elliptical.

*Division*.—Simple.

*Apex*.—Acute.

*Base*.—Cunneate.

*Venation*.—Pinnate.

*Vein color* (*adaxial surfaces*).—147A.

*Vein color* (*abaxial surfaces*).—137A.

*Margins*.—Mature margin is entire; immature margin is ciliate.

*Arrangement*.—Alternate.

*Attachment*.—Sessile.

*Texture*.—Leathery.

*Surfaces* (*adaxial surface*).—Juvenile: highly pubescent; mature: Finely pubescent to glabrous.

*Surfaces* (*abaxial surface*).—Juvenile: highly pubescent; mature: Finely pubescent to glabrous.

*Mature leaf dimensions*.—Average length 47 mm, average width 9 mm.

*Leaf color* (*adaxial surface*).—Juvenile: a mix of 144A and 152A; mature: 147A.

*Leaf color* (*abaxial surface*).—Juvenile: a mix of 144A and 152A; mature: a slightly darker hue of 147A in comparison with the adaxial surface.

*Petiole*.—None.

*Stipules*.—None.

Inflorescence:

*Inflorescence*.—Indeterminate, leafy spikes with an overall length of approximately 12 to 14 cm and a width of 5 to 7 cm, comprised of many small sessile florets with exserted stamens. Blooming period is spring.

*Flowers*.—Sessile. Sepals are immeasurably minute. Inconspicuous corolla comprised of five unfused petals; diameter across corolla is 6 to 9 mm (average of 7.6 mm). Color of the corolla approximates to yellow-green (RHS 154C or 154D). Non fragrant. Flowers of *Callistemon* are distinguished by their brightly colored, exserted stamen which give the spike a bottlebrush appearance.

*Bud*.—Many tightly grouped oblong axillary buds measuring approximately 6 to 9 mm long and 3 mm wide, at the widest point, prior to bud break. Color approximates to yellow-green 146C, prior to bud swell.

Reproductive organs:

*Stamens*.—Many; greater than 50.

*Stamen color*.—42A.

*Stamen dimensions*.—19 to 21 mm in length (average length is 19.6 mm) and very thin.

*Attachment*.—Each stamen joins floral tube independently: Free.

*Anther dimensions*.—Minute.

*Anther color*.—Yellow.

*Pollen*.—Present.

*Pistil*.—One.

*Pistil dimensions*.—About 20 mm in length and very thin.

*Pistil color*.—42A.

*Ovary position*.—Half-Inferior.

Fruit and seed production: Dehescent flowers reveal round, slightly oblong seed capsules grouped tightly along the stem. Sessile. Dimensions are 3 to 5 mm in diameter and 4 to 5 mm in length. Color at maturity approximates to brown 200A. Seeds are many and minute with a color close to greyed orange 166B.

COMPARISONS WITH OTHER *CALLISTEMON*

'LC01' is characterized by the combination of a short to medium height, large leaves, deep green foliage, and large inflorescence when compared to that of the parent plants, other seedling accessions from the same parent cross as well as other cultivars known to the breeder. There are two commercially available cultivars, known to the breeder, that have a similar form as 'LC01': *Callistemon viminalis* 'Matthew Flinders' (U.S. Plant Pat. No. 17,314) and *Callistemon viminalis* 'Lithe John' (unpatented).

Both 'Matthew Flinders' and 'Little John' are short *Callistemon* cultivars with an approximate height and width of 1 m whereas 'LC01' is larger with a height of approximately 1.8 m and a spread of 1.5 m. The foliage of 'LC01' is larger than both that of 'Matthew Flinders' and 'Little John' which gives 'LC01' a more dense and compact habit. 'Matthew Flinders' has foliage dimensions of 32 mm long and 6 mm wide whereas 'LC01' has much larger foliage that measures 47 mm long and 9 mm wide; the foliage of 'Little John' is closer in size to 'LC01' yet still smaller, measuring 39 mm in length and 8 mm wide. The foliage of 'LC01' is deep hue of yellow green (RHS 147A) whereas the foliage of 'Matthew Flinders' has a lighter green hue (RHS 137A) and the foliage of 'Little John' is greyed green 189A. This difference in foliage color gives 'LC01' a very healthy appearance by comparison to both 'Matthew Flinders' and 'Little John'.

The flower habit of 'LC01' is also easily distinguishable from that of 'Matthew Flinders' and 'Little John'. The inflorescence 'LC01' is comprised of approximately 75 florets that measures approximately 12 to 14 cm in length whereas the inflorescence of both 'Matthew Flinders' and 'Little John' are significantly smaller, measuring approximately 4 to cm long and containing only 15 to 25 florets. The stamen of 'LC01', as previously described above, are a lighter hue of red (corresponding to RHS 42A) when compared to the stamen of 'Matthew Flinders' and 'Little John' which are red 46B.

That which is claimed is:

1. A new and distinct variety of *Callistemon viminalis* plant named 'LC01', substantially as described and illustrated herein.

* * * * *